(12) United States Patent
Wu

(10) Patent No.: US 7,066,013 B2
(45) Date of Patent: Jun. 27, 2006

(54) HARDNESS TESTER

(76) Inventor: Shaoming Wu, 1846 Rd Robin Pl., Thousand Oaks, CA (US) 91320

( * ) Notice: Subject to any disclaimer, the term of this patent is extended or adjusted under 35 U.S.C. 154(b) by 179 days.

(21) Appl. No.: 10/724,500

(22) Filed: Dec. 1, 2003

(65) Prior Publication Data
US 2005/0115310 A1    Jun. 2, 2005

(51) Int. Cl.
*G01N 3/34* (2006.01)
(52) U.S. Cl. ......................................................... 73/82
(58) Field of Classification Search .............. 73/81–84, 73/12.09, 12.13
See application file for complete search history.

(56) References Cited

U.S. PATENT DOCUMENTS

| 1,544,332 A | * | 6/1925 | Mance | 73/78 |
| 2,372,662 A | * | 4/1945 | Dewey | 73/81 |
| 2,956,432 A | * | 10/1960 | Henrikson | 73/81 |
| 3,696,662 A | * | 10/1972 | Foltz et al. | 73/81 |
| 4,196,616 A | * | 4/1980 | Argabrite et al. | 73/81 |
| 4,245,496 A | * | 1/1981 | Napetschnig | 73/83 |
| 4,262,525 A | * | 4/1981 | Ernst | 73/81 |
| 4,534,212 A | * | 8/1985 | Targosz | 73/83 |

\* cited by examiner

*Primary Examiner*—Robert Raevis
(74) *Attorney, Agent, or Firm*—Raymond Y Chan; David and Raymond Patent Group

(57) ABSTRACT

A hardness tester includes a supporting frame having a guiding channel, a driving axle slidably disposed in the supporting frame, and a penetrating pin, having a pin head, coaxially disposed in the guiding channel in a slidably movable manner to coaxially align with the driving axle for the pin head to penetrate on a testing surface of a tested object. A linear displacement device includes a transmission shaft movably disposed in the supporting frame at a position universally contacting between the driving axle and the penetrating pin, and a displacement sensor supported at the transmission shaft, wherein when the driving axle is driven for applying a penetrating force to the penetrating pin through the transmission shaft, the linear sensor detects a linear displacement of the transmission shaft with respect to the penetrating pin for measuring the hardness of the tested object.

16 Claims, 4 Drawing Sheets

HARDNESS TESTER

BACKGROUND OF THE PRESENT INVENTION

1. Field of Invention

The present invention relates to a material hardness measuring device, and more particularly to a hardness tester, which allows the user to precisely measure the hardness of the material having a limited testing surface thereof.

2. Description of Related Arts

Hand-operated portable hardness meters are already known wherein a conventional hardness meter generally comprises a supporting frame having a flat supporting platform and an actuating gun comprising a driving pin slidably to align with the supporting platform in such a manner that when the testing material is positioned between the supporting platform and the driving pin, a penetrating force of the driving pin is exerted on the testing material so as to determine the hardness of the testing material through the penetrating force. Accordingly, the penetrating force includes a major loading force and a minor loading force wherein the result of the hardness test is determined by the depth of the indention on the testing material with respect to the minor loading force. However, such conventional hardness meter has several drawbacks.

In order to align the testing material between the supporting platform and the driving pin to test the hardness of the testing material, the testing material must provide a flat testing surface for the driving pin to penetrate thereon and a flat supporting surface to bias against the supporting platform. Accordingly, the testing surface and the supporting surface of the testing material must be flat and parallel with each other. Therefore, the testing material having an irregular shaped cannot be tested by such convention hardness meter. Otherwise, the test result of the hardness of the testing material will not accurate due to the uneven testing surface or the uneven supporting surface of the testing material.

Moreover, in order to measure the hardness of the testing material, the actuating gun generally comprises a force sensor angularly detect a linear displacement of the driving pin for determining the penetrating force of the driving pin, such that the force sensor is arranged to read the penetrating force of the driving pin by converting the linear displacement of the driving pin into an angular movement. In other words, the linear displacement of the driving pin is detected and converted to an angular displacement through a L-shaped measuring arm of the force sensor. Therefore, the test result may not precise due to the mechanical deviation of the force sensor.

Alternatively, the measurement device is arranged to read the penetrating force of the driving pin through a compression spring to convert the linear displacement of the driving pin by means of the spring compression force. Accordingly, the penetrating force of the driving pin is converted to the spring compression force by determining the spring coefficient. However, it is known that the compression spring will be deteriorated after a period of time. In other words, both conventional measurement devices of the hardness meter cannot precisely determine the hardness of the testing material due to the mechanical deviation.

SUMMARY OF THE PRESENT INVENTION

A main object of the present invention is to provide a hardness tester, which allows the user to precisely measure the hardness of the material having a limited testing surface thereof.

Another object of the present invention is to provide a hardness tester, which comprises a driving axle coaxially aligned with a penetrating pin, and a transmission shaft physically contacted between the driving axle and the penetrating pin for transmitting the penetrating force from the driving axle to the penetrating pin so as to minimize the error of the test result through the testing operation due to the unwanted lateral movement of the driving axle.

Another object of the present invention is to provide a hardness tester, wherein no supporting surface of the testing material is required during the testing operation of the hardness tester of the present invention so as to minimize the error of the test result through the testing operation due to the irregular shape of the testing material.

Another object of the present invention is to provide a hardness tester, which comprises a displacement sensor for detecting a linear displacement of the penetrating pin by means of electric capacity, so as to precisely measure the hardness of the material.

Another object of the present invention is to provide a hardness tester, wherein the displacement sensor is supported by the transmission shaft to detect the linear displacement of the penetrating pin so as to enhance the accuracy of the test result.

Another object of the present invention is to provide a hardness tester, wherein the force sensor is operated independently with the penetrating pin so as to prevent the force sensor from being damage by the reaction of the penetrating force of the penetrating pin.

Another object of the present invention is to provide a hardness tester, which can incorporate with a supporting arm having a supporting platform to bias against the supporting surface of the testing material for enhancing the testing operation, wherein the supporting platform is adapted to be selectively adjusted to fit on the supporting surface of the testing material so that the testing material having an uneven supporting surface with respect to the testing surface can be tested by the hardness tester of the present invention.

Another object of the present invention is to provide a hardness tester constructed as a hand-operated portable hardness meter which is advantage in practice use.

Accordingly, in order to accomplish the above objects, the present invention provides a hardness tester for measuring a hardness of a tested object having a testing surface, comprising:

a supporting frame having a receiving chamber and an elongated guiding channel coaxially extended to communicate with the receiving chamber;

a driving axle slidably disposed in the receiving chamber of the supporting frame;

a penetrating pin, having a pin head, coaxially disposed in the guiding channel in a slidably movable manner to coaxially align with the driving axle for the pin head to penetrate on the testing surface of the tested object; and a linear displacement device, comprising a transmission shaft movably disposed in the receiving chamber at a position universally contacting between the driving axle and the penetrating pin, and a displacement sensor supported at the transmission shaft, wherein when the driving axle is driven for applying a penetrating force to the penetrating pin through the transmission shaft, the linear sensor detects a linear displacement of the transmission shaft with respect to the penetrating pin for measuring the hardness of the tested object.

These and other objectives, features, and advantages of the present invention will become apparent from the following detailed description, the accompanying drawings, and the appended claims.

DETAILED DESCRIPTION OF THE PREFERRED EMBODIMENT

Figure 1:
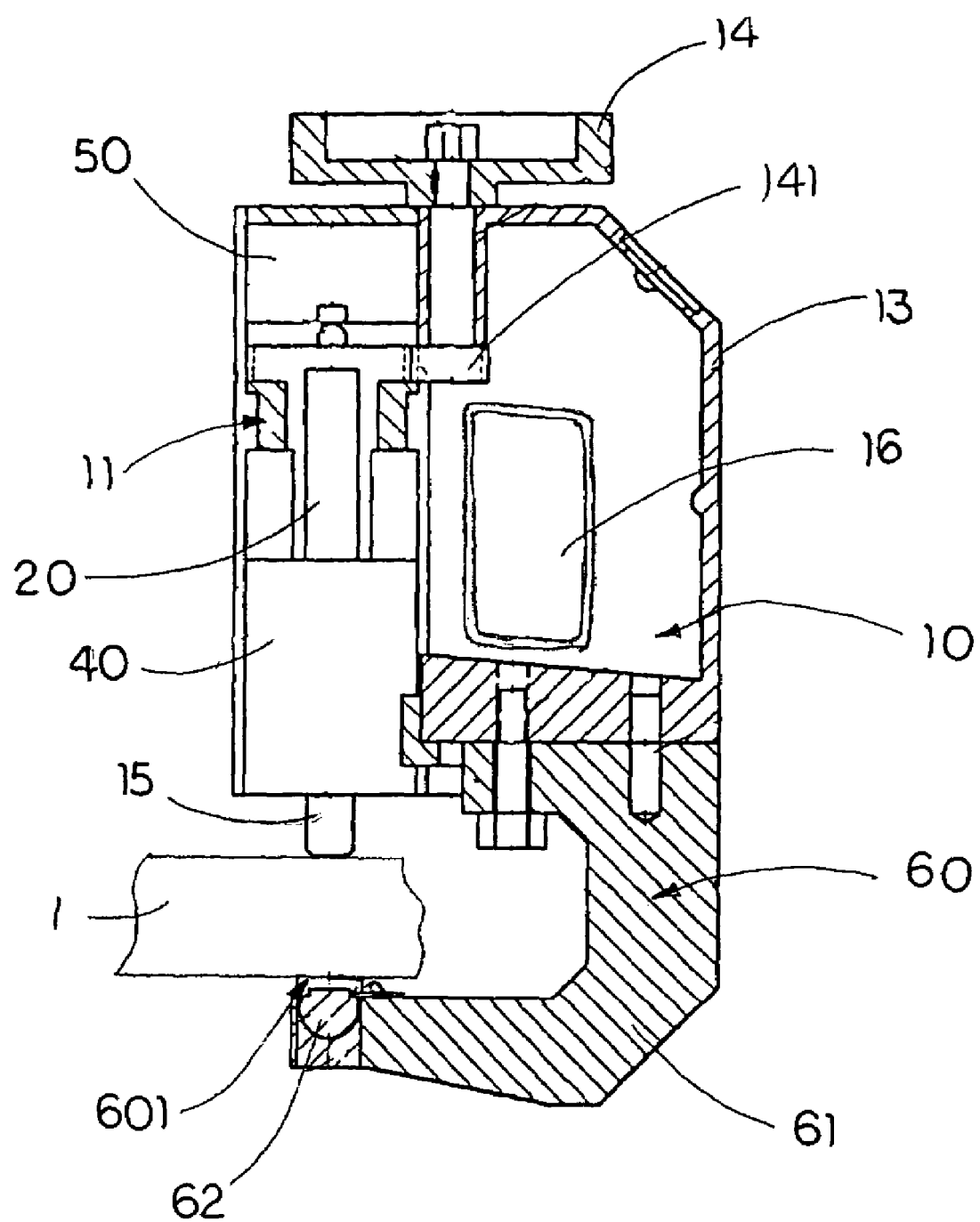
FIG. 1 is a sectional view of the hardness tester according to a preferred embodiment of the present invention.
Figure 2:
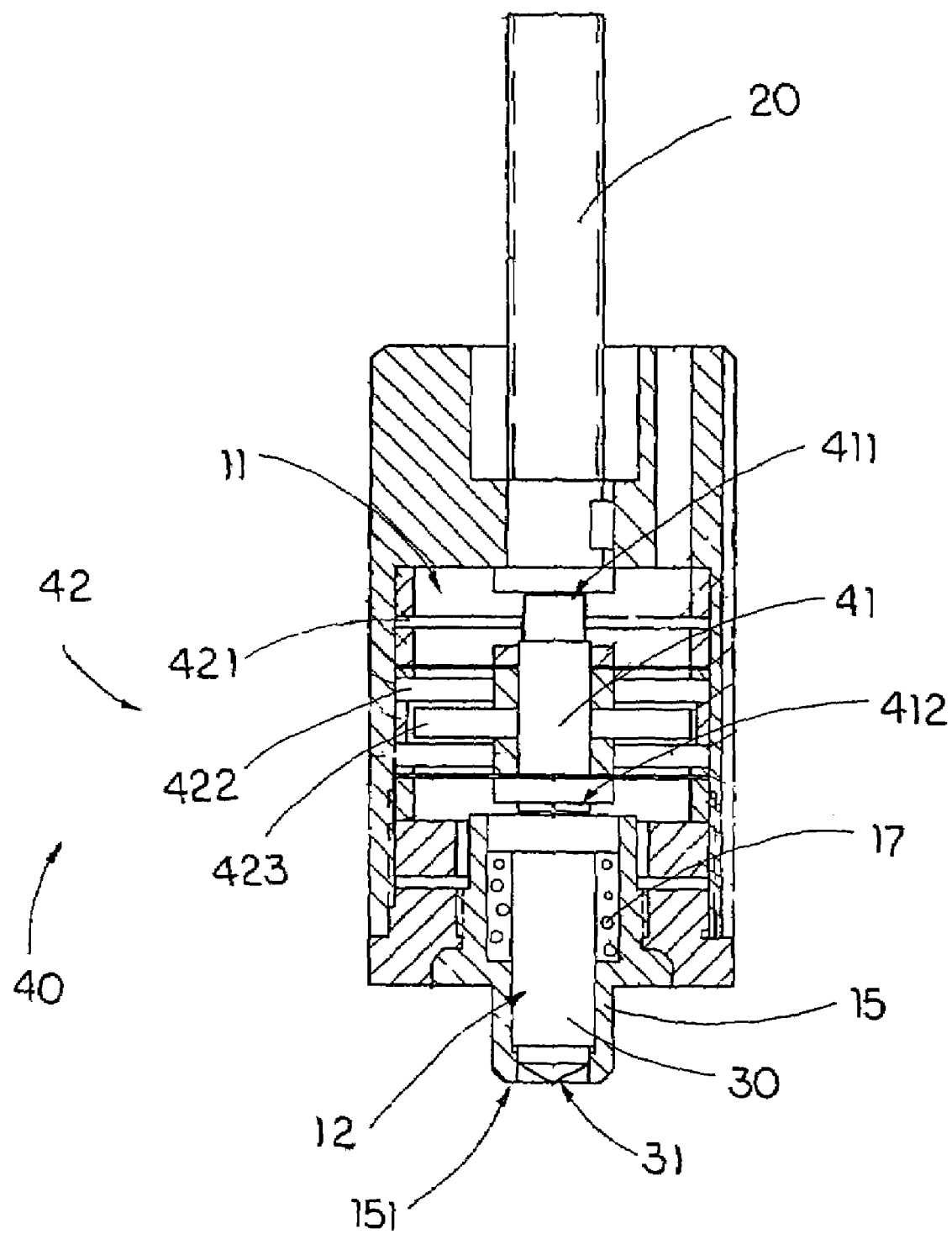
FIG. 2 is a sectional view of the linear displacement device of the hardness tester according to the above preferred embodiment of the present invention.

Referring to FIGS. 1 and 2 of the drawings, a hardness tester according to a preferred embodiment of the present invention is illustrated, wherein the hardness tester is adapted for measuring a hardness of a tested object 1 having a testing surface.

The hardness tester comprises a supporting frame 10 having a receiving chamber 11 and an elongated guiding channel 12 coaxially extended to communicate with the receiving chamber 11, a driving axle 20 slidably disposed in the receiving chamber 11 of the supporting frame 10, and a penetrating pin 30 coaxially disposed in the guiding channel 12 in a slidably movable manner to coaxially align with the driving axle 20 for the pin head 31 to penetrate on the testing surface of the tested object 1.

The hardness tester further comprises a linear displacement device 40 which comprises a transmission shaft 41 movably disposed in the receiving chamber 11 at a position universally contacting between the driving axle 20 and the penetrating pin 30, and a displacement sensor 42 supported by the transmission shaft 41, wherein when the driving axle 20 is driven for applying a penetrating force to the penetrating pin 30 through the transmission shaft 41, the linear sensor 42 detects a linear displacement of the transmission shaft 41 with respect to the penetrating pin 30 for measuring the hardness of the tested object 1.

According to the preferred embodiment, the supporting frame 10, which is made of rigid material such as metal, comprises a hand-held casing 13 defining the receiving chamber 11 therein, a driving wheel 14 rotatably mounted to the hand-held casing 13 for applying the penetrating force on the driving axle 20 via a gear unit 141, and a tubular guiding cylinder 15 which is extended from the hand-held casing 13 and defines the guiding channel 12, wherein an opening edge 151 of the guiding cylinder 15 is arranged for biasing against the testing surface of the tested object 1 to guide the pin head 31 of the penetrating pin 30 to penetrated thereon.

As shown in FIG. 2, the opening edge 151 of the guiding cylinder 15 has a flat surface for substantially biasing against the testing surface of the tested object 1 in such a manner that the opening edge 151 of the guiding cylinder 15 functions as a guiding surface to guide the pin head 31 of the penetrating pin 30 for perpendicularly penetrating on the testing surface of the tested object 1.

Therefore, the tested object 1 requires a relatively small testing surface in a flat manner that enough the opening edge 151 of the guiding cylinder 15 to bias thereon in such a manner that the penetrating pin 30 is guided to coaxially slide along the guiding channel 12 of the guiding cylinder 15 to precisely penetrate the pin head 31 at the testing surface of the tested object 1.

The supporting frame 10 further comprises a resilient element 17 disposed within the guiding channel 12 for applying an urging force against the penetrating pin 30 to retain the penetrating pin 30 in a normal testing position. The resilient element 17, according to the preferred embodiment, is a compression spring coaxially mounted to the penetrating pin 30 wherein the resilient element 17 has two ends biasing against the penetrating pin 30 and an inner wall of the guiding channel 12 respectively to slidably push the penetrating pin 30 within the guiding channel 12.

Accordingly, while releasing the penetrating force after the penetrating pin 30 is pushed to slidably extend the pin head 31 thereof out of the guiding channel 12 at the opening edge 151 for penetrating on the testing surface of the tested object 1, the compressed resilient element 17 is rebounded to slidably push the penetrating pin 30 back into the guiding channel 12.

As shown in FIG. 2, the transmission shaft 41 has a driven end 411 universally contacting with the driving axle 20 and a driving end 412 universally contacting with the penetrating pin 30 wherein the transmission shaft 41 is adapted for transmitting the penetrating force from the driving shaft 20 to the penetrating pin 30. Accordingly, when the penetrating force is applied on the driving axle 20 to drive the driving axle to slidably move forward, the penetrating pin 30 is pushed to slide the pin head 31 thereof out of the opening edge 151 of the guiding channel 12 through the transmission shaft 41. It is worth to mention that when the driving wheel 14 applies the penetrating force on the driving axle 20, an unwanted lateral movement of the driving axle 20 may be created. As a result, the actual linear displacement of the penetrating pin 30 cannot be detected. However, when the penetrating force is transmitted to the penetrating pin 30 through the transmission shaft 41, the transmission shaft 41 is adapted to minimize the unwanted lateral movement of the driving axle 20 to the penetrating pin 30, so as to enhance the detection of the linear displacement of the penetrating pin 30 with respect to the test object 1.

Accordingly, when the penetrating force is applied on the driving axle 20, the transmission shaft 41 transmits the penetrating force as a downward pushing force to slidably push the pin head 31 of the penetrating pin 30 out of the opening edge 151 of the guiding channel 12, such that even if the driving axle 20 is not precisely align with the penetrating pin 30 in a coaxial manner, the transmission shaft 41 is adapted to adjust the penetrating force to push the penetrating pin 30 to coaxially slide along the guiding channel 12 for penetrating on the testing surface of the tested object 1 so as to enhance the accuracy of the test result.

The displacement sensor 42 comprises a linear sensor circuit 421 supported within the receiving chamber 11 and first and second linear sensor terminals 422, 423 electrically coupling with the sensor circuit 421 and the transmission shaft 41 respectively in such a manner that when the transmission shaft 41 is driven to move within the receiving chamber 11, the linear sensor circuit 421 detects the linear displacement of the transmission shaft 41 with respect to a positioning differentiation between the linear first and second terminals 422, 423.

It is worth to mention that the linear displacement of the transmission shaft 41 is corresponding to a linear displacement of the penetrating pin 30 that the pin head 31 is penetrated on the testing surface of the tested object 1 because the penetrating force is transmitted to the penetrating pin 30 through the transmission shaft 41. Therefore, by detecting the linear displacement of the transmission shaft 41, the hardness result of the tested object can be measured via the penetrating force.

In addition, since the transmission shaft 41 is universally contacted between the driving axle 20 and the penetrating pin 30 for transmitting the penetrating force thereto, the penetrating force does not directly exert to the displacement sensor 42 so as to prevent the displacement sensor 42 from being damage due to the penetrating force.

Figure 3:
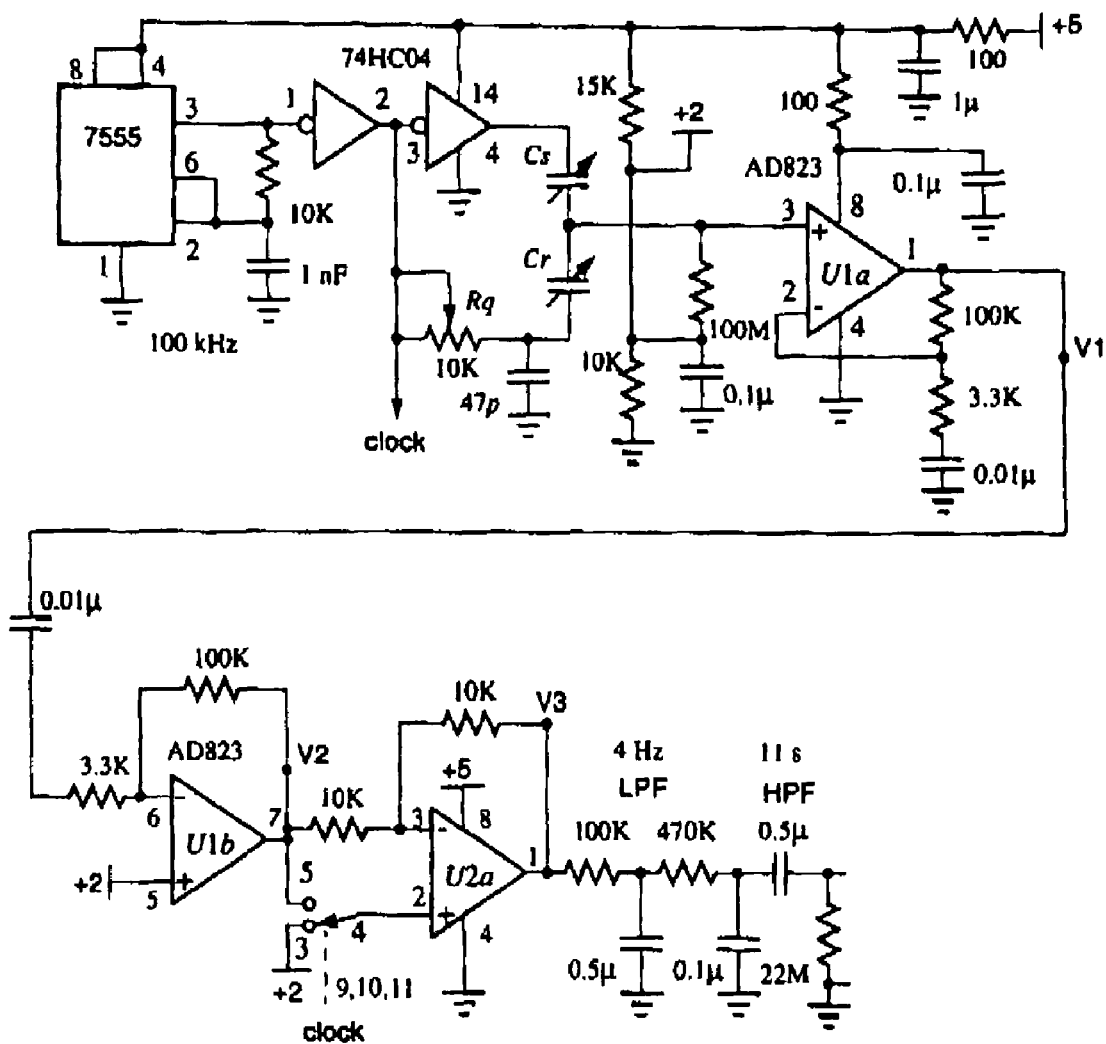
FIG. 3 is a circuit diagram of the linear sensor circuit of the hardness tester according to the above preferred embodiment of the present invention.
Figure 4:
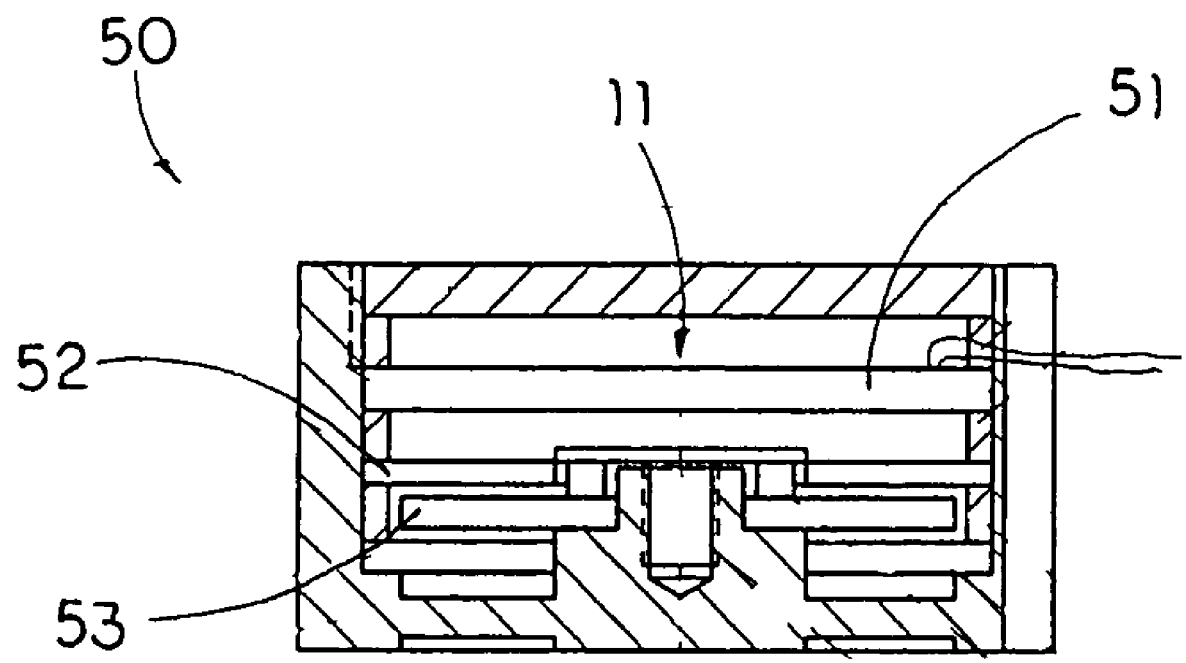
FIG. 4 is a sectional view of a force sensor of the hardness tester according to the above preferred embodiment of the present invention.

As shown in FIG. 4, the hardness tester further comprises a force sensor 50 supported within the receiving chamber 11 to couple with the driving axle 20 for detecting the penetrating force thereon. The force sensor 50, such as a load cell, comprises a force sensor circuit 51 supported at the receiving chamber 11 and first and second force sensor terminals 52, 53 electrically coupling with the force sensor circuit 51 and the driving axle 20 respectively, in such a manner that the force sensor circuit 51 is adapted for detecting the penetrating force on the driving axle 20 with respect to a positioning differentiation between the first and second force sensor terminals 52, 53. Therefore, when the penetrating force of the driving axle 20 and the linear displacement of the penetrating pin 30 are respectively detected by the force sensor 50 and the displacement sensor 42, the hardness of the tested object 1 can be measured through the hardness measuring circuit as shown in FIG. 3.

As shown in FIG. 1, the supporting frame 10 further comprises a display screen 16 electrically connected between the force sensor 50 and the displacement sensor 42 for displaying the test result of the tested object 1 via the hardness measuring circuit through the penetrating force of the driving axle 20 and the linear displacement of the penetrating pin 30.

The hardness tester further comprises a retaining frame 60 extended from the supporting frame 10, wherein the retaining frame 60 has a supporting platform 601 adjustably aligned with the pin head 31 of the penetrating pin 30 for substantially retaining the opening edge 151 of the guiding channel 12 at the testing surface of the tested object 1.

As shown in FIG. 1, the retaining frame 60 comprises a retaining arm 61 having a L-shaped extended from the supporting frame 10 and a supporting member 62 which defines the supporting platform 601 thereon and is mounted at a free end of the retaining arm 61 in a rotatably movable manner such that the opening edge 151 of the guiding channel 12 and the supporting platform 601 are adapted for substantially biasing against the tested object 1 to align the pin head 31 of the penetrating pin 30 with the testing surface of the tested object 1.

Accordingly, the supporting member 62 has a spherical bottom portion rotatably mounted to the free end of the retaining arm 61 to rotatably adjust the supporting platform 601 for fittingly biasing against the tested object 1. It is worth to mention that the retaining arm 61 is detachably attached to the supporting frame 10 to support the supporting member 62 so as to retain a distance between the opening edge 151 of the guiding channel 12 and the supporting platform 601. Therefore, the user is able to select a corresponding size of the retaining arm 61 with respect to the thickness of the tested object 1 such that the tested object 1 can be substantially held between the opening edge 151 of the guiding channel 12 and the supporting platform 601 in position.

It is worth to mention that the testing surface and the supporting surface of the tested object 1 must be flat and parallel with each other for the conventional hardness measuring device. However, the supporting platform 601 can be selectively adjust to bias against the supporting surface of the tested object 1 such that the tested object 1 having an irregular shaped can be tested by the hardness tester of the present invention.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A hardness tester for measuring a hardness of a tested object having a testing surface, comprising:

a supporting frame comprising a hand-held casing having a receiving chamber, a driving wheel rotatably mounted to said hand-held casing, and a tubular guiding cylinder having an elongated guiding channel extended from said hand-held casing at a position that said guiding channel is coaxially extended to communicate with said receiving chamber;

a driving axle slidably disposed in said receiving chamber of said supporting frame;

a gear unit supported in said hand-held casing to operatively couple said driving wheel with said driving axle in such a manner that when said driving wheel is rotated, said driving wheel is adapted for applying a penetrating force on said driving axle through said gear unit;

a penetrating pin, having a pin head, coaxially disposed in said guiding channel in a slidably movable manner to coaxially align with said driving axle for said pin head to penetrate on said testing surface of said tested object; and a linear displacement device, comprising a transmission shaft slidably disposed in said receiving chamber to end-to-end contact between said driving axle and said penetrating pin, and a displacement sensor supported in said receiving chamber for detecting a linear displacement of said transmission shaft, wherein when said transmission shaft transmits said penetrating force from said driving axle to said penetrating pin, said linear sensor detects said linear displacement of said transmission shaft in response to said penetrating pin for measuring, said hardness of said tested object.

2. The hardness tester, as recited in claim 1, wherein an opening edge of said guiding cylinder has a flat surface for substantially biasing against said testing surface of said tested object in such a manner that said opening edge of said guiding cylinder functions as a guiding surface to guide said pin head of said penetrating pin for perpendicularly penetrating on said testing surface of said tested object.

3. The hardness tester, as recited in claim 1, wherein said displacement sensor comprises a linear sensor circuit supported within said receiving chamber and first and second linear sensor terminals electrically coupling with said sensor circuit and said transmission shaft respectively in such a manner that when said transmission shaft is driven to move within said receiving chamber, said linear sensor circuit detects said linear displacement of said transmission shaft with respect to a positioning differentiation between said linear first and second terminals.

4. The hardness tester, as recited in claim 2, wherein said displacement sensor comprises a linear sensor circuit supported within said receiving chamber and first and second linear sensor terminals electrically coupling with said sensor circuit and said transmission shaft respectively in such a manner that when said transmission shaft is driven to move within said receiving chamber, said linear sensor circuit detects said linear displacement of said transmission shaft with respect to a positioning differentiation between said linear first and second terminals.

5. The hardness tester, as recited in claim 1, wherein said transmission shaft has a driven end contacting with said driving axle and a driving end contacting with said penetrating pin, wherein the transmission shaft is adapted for transmitting said penetrating force from said driving shaft as a pushing force to slidably push said penetrating pin to coaxially slide along said guiding channel for said pin head of said penetrating pin penetrating on said testing surface of said tested object.

6. The hardness tester, as recited in claim 2, wherein said transmission shaft has a driven end contacting with said driving axle and a driving end contacting with said penetrating pin, wherein the transmission shaft is adapted for transmitting said penetrating force from said driving shaft as a pushing force to slidably push said penetrating pin to coaxially slide along said guiding channel for said pin head of said penetrating pin penetrating on said testing surface of said tested object.

7. The hardness tester, as recited in claim 4, wherein said transmission shaft has a driven end contacting with said driving axle and a driving end contacting with said penetrating pin, wherein the transmission shaft is adapted for transmitting said penetrating force from said driving shaft as a pushing force to slidably push said penetrating pin to coaxially slide along said guiding channel for said pin head of said penetrating pin penetrating on said testing surface of said tested object.

8. The hardness tester, as recited in claim 1, further comprising a force sensor supported within said receiving chamber to couple with said driving axle for detecting said penetrating force thereon, wherein said force sensor comprises a force sensor circuit supported at said receiving chamber and first and second force sensor terminals electrically coupling with said force sensor circuit and said driving axle respectively, in such a manner that said force sensor circuit is adapted for detecting said penetrating force on said driving axle with respect to a positioning differentiation between said first and second force sensor terminals.

9. The hardness tester, as recited in claim 4, further comprising a force sensor supported within said receiving chamber to couple with said driving axle for detecting said penetrating force thereon, wherein said force sensor comprises a force sensor circuit supported at said receiving chamber and first and second force sensor terminals electrically coupling with said force sensor circuit and said driving axle respectively, in such a manner that said force sensor circuit is adapted for detecting said penetrating force on said driving axle with respect to a positioning differentiation between said first and second force sensor terminals.

10. The hardness tester, as recited in claim 7, further comprising a force sensor supported within said receiving chamber to couple with said driving axle for detecting said penetrating force thereon, wherein said force sensor comprises a force sensor circuit supported at said receiving chamber and first and second force sensor terminals electrically coupling with said force sensor circuit and said driving axle respectively, in such a manner that said force sensor circuit is adapted for detecting said penetrating force on said driving axle with respect to a positioning differentiation between said first and second force sensor terminals.

11. The hardness tester, as recited in claim 2, further comprising a retaining frame extended from said supporting frame, wherein said retaining frame has a supporting platform adjustably aligned with said pin head of said penetrating pin for substantially retaining said opening edge of said guiding channel at said testing surface of said tested object.

12. The hardness tester, as recited in claim 7, further comprising a retaining frame extended from said supporting frame, wherein said retaining frame has a supporting platform adjustably aligned with said pin head of said penetrating pin for substantially retaining said opening edge of said guiding channel at said testing surface of said tested object.

13. The hardness tester, as recited in claim 10, further comprising a retaining frame extended from said supporting frame, wherein said retaining frame has a supporting platform adjustably aligned with said pin head of said penetrating pin for substantially retaining said opening edge of said guiding channel at said testing surface of said tested object.

14. The hardness tester, as recited in claim 11, wherein said retaining frame comprises a retaining arm having a L-shape extended from said supporting frame and a supporting member which defines said supporting platform thereon and has a spherical bottom portion mounted at a free end of said retaining arm in a rotatably movable manner such that said opening edge of said guiding channel and said supporting platform are adapted for substantially biasing against said tested object to align said pin head of said penetrating pin with said testing surface of said tested object.

15. The hardness tester, as recited in claim 12, wherein said retaining frame comprises a retaining arm having a L-shape extended from said supporting frame and a supporting member which defines said supporting platform thereon and has a spherical bottom portion mounted at a free end of said retaining arm in a rotatably movable manner such that said opening edge of said guiding channel and said supporting platform are adapted for substantially biasing against said tested object to align said pin head of said penetrating pin with said testing surface of said tested object.

16. The hardness tester, as recited in claim 13, wherein said retaining frame comprises a retaining arm having a L-shape extended from said supporting frame and a supporting member which defines said supporting platform thereon and has a spherical bottom portion mounted at a free end of said retaining arm in a rotatably movable manner such that said opening edge of said guiding channel and said supporting platform are adapted for substantially biasing against said tested object to align said pin head of said penetrating pin with said testing surface of said tested object.

* * * * *